US 6,652,576 B1

(12) United States Patent
Stalker

(10) Patent No.: US 6,652,576 B1
(45) Date of Patent: Nov. 25, 2003

(54) VARIABLE STIFFNESS STENT

(75) Inventor: Kent C. B. Stalker, San Marcos, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/590,307

(22) Filed: Jun. 7, 2000

(51) Int. Cl.⁷ .................................................. A61F 2/06
(52) U.S. Cl. ..................... 623/1.18; 623/1.15; 606/194; 606/198
(58) Field of Search ................................. 428/596, 610; 148/402, 902, 909, 563, 564; 623/1.18, 1.19, 1.15; 606/194, 195, 198

(56) References Cited

U.S. PATENT DOCUMENTS

| 4,484,955 A | * | 11/1984 | Hochstein | 148/11.5 R |
| 4,881,981 A | | 11/1989 | Thoma et al. | 148/11.5 R |
| 4,922,718 A | * | 5/1990 | Hochstein et al. | 60/527 |

(List continued on next page.)

FOREIGN PATENT DOCUMENTS

| EP | 0 800 801 A1 | 10/1997 |
| EP | 0 830 853 A1 | 3/1998 |
| WO | WO 98/22159 | 5/1998 |
| WO | WO 98/48734 | 11/1998 |
| WO | WO 01/08600 A2 * | 2/2001 |

OTHER PUBLICATIONS

Schetky, L. McDonald, "Shape Memory Alloys," *Scientific American*, vol. 281, pp. 74–82 (Nov. 1979).
Gupta, Subash, et al., *Effect of Cold Work on Mechanical Properties and on TTR's of a Nickel Titanium Shape Memory Alloy*, Proceedings of the Second International Conference on Shape Memory and Superelastic Technologies, Asilomar Conference Center, Pacific Grove, California pp. 41–46, 1997. (No month).
Duerig, T.W., et al., *An Engineer's Perspective of Pseudoelasticity*, Source Unknown, pp. 369–393, Undated.
Zadno, G.R., et al., *Linear Superelasticity in Cold–Worked Ni–Ti*, Source Unknown, pp. 414–419, Undated.

*Primary Examiner*—John J. Zimmerman
(74) *Attorney, Agent, or Firm*—Fulwider Patton Lee & Utecht, LLP

(57) ABSTRACT

A stent having a structure differentiated in terms of its stiffness. Such differentiation is achieved with the use of a superelastic material that transitions between a relatively soft and malleable phase to a stiffer phase at a transition temperature that is adjustable. By differentially adjusting the transition temperature of different portions of the stent, a differentiation of the stiffness of the structure is achieved upon the stent being subjected to body temperature.

38 Claims, 5 Drawing Sheets

U.S. PATENT DOCUMENTS

| | | | |
|---|---|---|---|
| 4,969,890 A | * 11/1990 | Sugita et al. | 606/192 |
| 5,017,133 A | * 5/1991 | Miura | 433/20 |
| 5,025,799 A | * 6/1991 | Wilson | 128/772 |
| 5,366,504 A | 11/1994 | Andersen et al. | 623/11 |
| 5,383,892 A | 1/1995 | Cardon et al. | 606/198 |
| 5,395,390 A | 3/1995 | Simon et al. | 606/198 |
| 5,413,597 A | 5/1995 | Krajicek | 623/1 |
| 5,421,955 A | 6/1995 | Lau et al. | 216/48 |
| 5,449,373 A | 9/1995 | Pinchasik et al. | 606/198 |
| 5,476,506 A | 12/1995 | Lunn | 623/1 |
| 5,514,115 A | * 5/1996 | Frantzen et al. | 604/281 |
| 5,514,154 A | 5/1996 | Lau et al. | 606/195 |
| 5,569,295 A | 10/1996 | Lam | 600/198 |
| 5,601,593 A | * 2/1997 | Freitag | 606/198 |
| 5,674,276 A | 10/1997 | Andersen et al. | 623/1 |
| 5,716,393 A | 2/1998 | Lindenberg et al. | 623/1 |
| 5,836,966 A | 11/1998 | St. Germain | 606/198 |
| 5,855,600 A | 1/1999 | Alt | 623/1 |
| 5,861,027 A | 1/1999 | Trapp | 623/1 |
| 5,868,780 A | * 2/1999 | Lashinski et al. | 606/198 |
| 5,876,434 A | 3/1999 | Flomenblit et al. | |
| 5,904,657 A | * 5/1999 | Unsworth et al. | 600/585 |
| 5,911,754 A | 6/1999 | Kanesaka et al. | 623/1 |
| 5,922,021 A | 7/1999 | Jang | 623/1 |
| 5,938,697 A | 8/1999 | Killion et al. | 623/1 |
| 5,954,743 A | 9/1999 | Jang | 606/198 |
| 5,964,744 A | * 10/1999 | Balbierz et al. | 604/530 |
| 6,010,530 A | 1/2000 | Goicoechea | 623/1 |
| 6,027,526 A | 2/2000 | Limon et al. | 623/1 |
| 6,053,943 A | * 4/2000 | Edwin et al. | 623/1.25 |
| 6,066,168 A | 5/2000 | Lau et al. | 623/1.16 |
| 6,071,298 A | 6/2000 | Lashinski et al. | 606/198 |
| 6,106,548 A | 8/2000 | Roubin et al. | 623/115 |
| 6,106,642 A | * 8/2000 | DiCarlo et al. | 148/563 |
| 6,146,403 A | 11/2000 | St. Germain | 606/198 |
| 6,485,507 B1 | * 11/2002 | Walak et al. | 623/1.15 |

* cited by examiner

VARIABLE STIFFNESS STENT

BACKGROUND OF THE INVENTION

The present invention relates generally to vascular devices and more particularly, to expandable intraluminal vascular grafts that are usually referred to as stents. The invention is directed to the differentiation of the structural stiffness of such a device, including for example the localized variation of the stiffness of specific portions or elements of a stent.

Stents are used to maintain the patency of vessels in the body. They are typically advanced through the vasculature to the deployment site while in a contracted state where they are caused to expand so as to engage the vessel walls and allow the flow of fluid there through. Such stent can be moved along a guide wire previously positioned in the vessel and then expanded by retraction of a restraining sheath within which the stent is disposed. Subsequent removal of the deployment devices along with the guide wire leaves the stent in place and locked in its expanded state.

The prolonged presence of a foreign body within the bloodflow can, under certain circumstances, lead to a restenosis which would diminish and eventually vitiate the utility of the implanted stent. A restenosis could require cleaning of the stent, replacement of the stent or more drastic surgical intervention. It is of course desirable to minimize the occurrence of restenosis.

A number of different conditions have been found to effect the rate and the extent of restenosis. One such condition is prolonged or repeated trauma to the vessel tissue. In order to minimize such trauma, it is important to ensure that the stent engages the vessel walls very uniformly such that the supporting forces are uniformly distributed. This is often difficult to achieve at the extreme ends of the stent where the abrupt termination of the stent naturally provides for an uneven distribution of supporting forces. Additionally, the overall longitudinal stiffness of the stent may cause the ends of the stent to become excessively embedded in the vessel walls in the event a linearly shaped stent is forced to conform to a non-linear deployment site. A similar problem arises when the deployment site is tapered or extends across a bifurcation. A uniformly stiff stent which is configured and dimensioned to adequately support such vessel in the large end of the taper or the large portion of the bifurcation may exert excessive forces on the vessel walls in the small end of the taper or the smaller portion of the bifurcation. Any of the described conditions may cause sufficient trauma to be inflicted upon the vessel walls to induce restenosis.

Another identified cause of restenosis is the disruption of the flow of blood. Turbulence caused by such disruption can trigger any number of defense mechanisms by which the body reacts to such unnatural condition. The ends of a stent may again be the cause of such undesirable situation. Any non-conformance to the vessel walls at the extreme ends of the stent could cause portions thereof to project into the bloodflow and thereby cause a disruption. Alternatively, a stent may conceivably distort a lumen sufficiently to disrupt the smooth flow of blood there through.

Efforts to address these problems have previously focused upon variably configuring and dimensioning the struts and spines of the stent in order to reduce their stiffness near the ends of the stent and/or to reduce longitudinal stiffness while maintaining substantial radial strength. For example, by selecting the dimensions of the spines to be relatively smaller than the dimensions of the struts, the desired reduction in stiffniess and strength may be achievable. Alternatively, the width and/or thickness of the various structural components near the ends of the stent may be reduced relative to the width and thickness of the corresponding structural components near the center of the stent in order to decrease the relative stiffness of the stent ends. A similar approach could be taken to adapt a stent to a tapered or bifurcated deployment site. However, such approaches tend to substantially increase the complexity and cost of the manufacturing process. Each and every version of a stent would require its own tooling.

It is therefore most desirable to provide a stent configuration by which traumatization of the vessel walls and disruption of the blood flow is minimized. More particularly, a stent is needed having ends that have a reduced tendency to impinge into and become embedded in the vessel walls as well as to project into the blood stream. Moreover, it is most desirable to provide a manufacturing process by which the stiffniess of various components of the stent can be adjusted quickly and easily to suit the requirements of a particular type of application.

SUMMARY OF THE INVENTION

The present invention provides a vascular device that exhibits a differentiated degree of stiffness throughout selected portions of its structure. Such vascular device when in the form of a stent overcomes disadvantages associated with certain prior art stents in that it is capable of providing the necessary support to the vessel walls within which it is deployed without exerting undesirable forces thereon. In accordance with the present invention, the stiffness of the stent is readily differentiated throughout its structure in any of a number of configurations. The stent's stiffness may thereby be reduced in those areas where it is determined that support is less critical than avoidance of the traumatization of the tissue it is in contact with. Such stiffness differentiation is achieved with the differentiated heat treatment of selected portions or elements of the stent after its fabrication. This provides a further advantage in that a single stent structure can thereby be tailored to accommodate the specific requirements of many different types of deployment sites.

The desired differentiation in the stiffness of the stent of the present invention is achieved by the use of a superelastic material in its construction wherein such material undergoes a transition from a relatively soft and malleable phase to a relatively strong and stiff phase as the material's temperature is raised through a transition temperature. The phase transition is fully reversible. Approaching the transition temperature from below causes the material to become stronger and stiffer while approaching such temperature from above causes the material to become softer and more malleable. Heat treatment of the material serves to shift the transition temperature to a higher temperature. Heat treatment of isolated portions of the stent serves to shift the transition temperature of only those portions to a higher temperature. By shifting the transition temperature of selected portions of the stent closer to body temperature, i.e., to nearer the temperature at which the stent will be maintained after deployment, such portions while tend to be in a softer and more malleable state than those portions of the stent wherein the transition temperature has not been shifted or has been shifted to a lesser degree.

The desired differentiation may be achieved either by subjecting only those portions of the stent which are to be softer and more malleable to an elevated temperature or by subjecting the entire stent to an elevated temperature while maintaining those portions which are to remain strong and stiff in contact with a heat sink. Any of various heat sources can be used to supply the necessary heat energy in order to achieve a certain shift whereby the total heat energy that is supplied is a function of both the temperature and the total time of exposure to such temperature.

In one embodiment, the stent is heat treated such that the end portions of the stent are in a softer and more malleable state than its center portion when the stent is subsequently subjected to body temperature. The center portion of the stent is thereby able to provide the necessary support to the vessel wall while its ends are less likely to become excessively embedded in the vessel tissue. As a result, the risk of restenosis is reduced.

In an alternative embodiment, the stiffniess of only one end of the stent is reduced in order to enable the stent to more uniformly support a tapered deployment site or a deployment site that extends across a bifurcation. The change in stiffness may be relatively abrupt or may be distributed over a significant portion of the stent. By positioning the more malleable end of the stent in the smaller region of the vessel, traumatization of the vessel tissue is less likely. The risk of restenosis is thereby correspondingly reduced.

In a further alternative embodiment, the longitudinal stiffness of the entire stent is reduced without a reduction in its radial stiffness. This enables the entire stent to more uniformly conform to the vessel walls of a non-linear deployment site without compromising the stent's ability to support the vessel walls. The stent ends are therefore less likely to become excessively embedded in the vessel tissue to thus reduce the risk of restenosis.

The superelastic material preferred for use in the present invention is nitinol. The temperature at which the transition from the relatively soft and malleable martensitic phase to the relatively strong and stiff austenitic phase is completed is commonly referred to as the A(f). A 10° C. to 30° C. shift in the A(f) can yield a difference in stiffness of up to about 50%.

These and other features and advantages of the present invention will become apparent from the following detailed description of a preferred embodiments which, taken in conjunction with the accompanying drawings, illustrate by way of example the principles of the invention.

DETAILED DESCRIPTION OF THE PREFERRED EMBODIMENTS

The vascular device of the present invention exhibits a differentiated degree of stiffness at selected locations in its structure. In the case of a stent, such differentiation may be limited to the longitudinal stiffness versus the radial stiffniess of the stent or may include both longitudinal as well as radial stiffness differentiation in certain areas of its structure. The invention allows a fabricated stent's stiffness characteristics to be tailored to more effectively accommodate specific types of deployment sites.

Figure 1A:
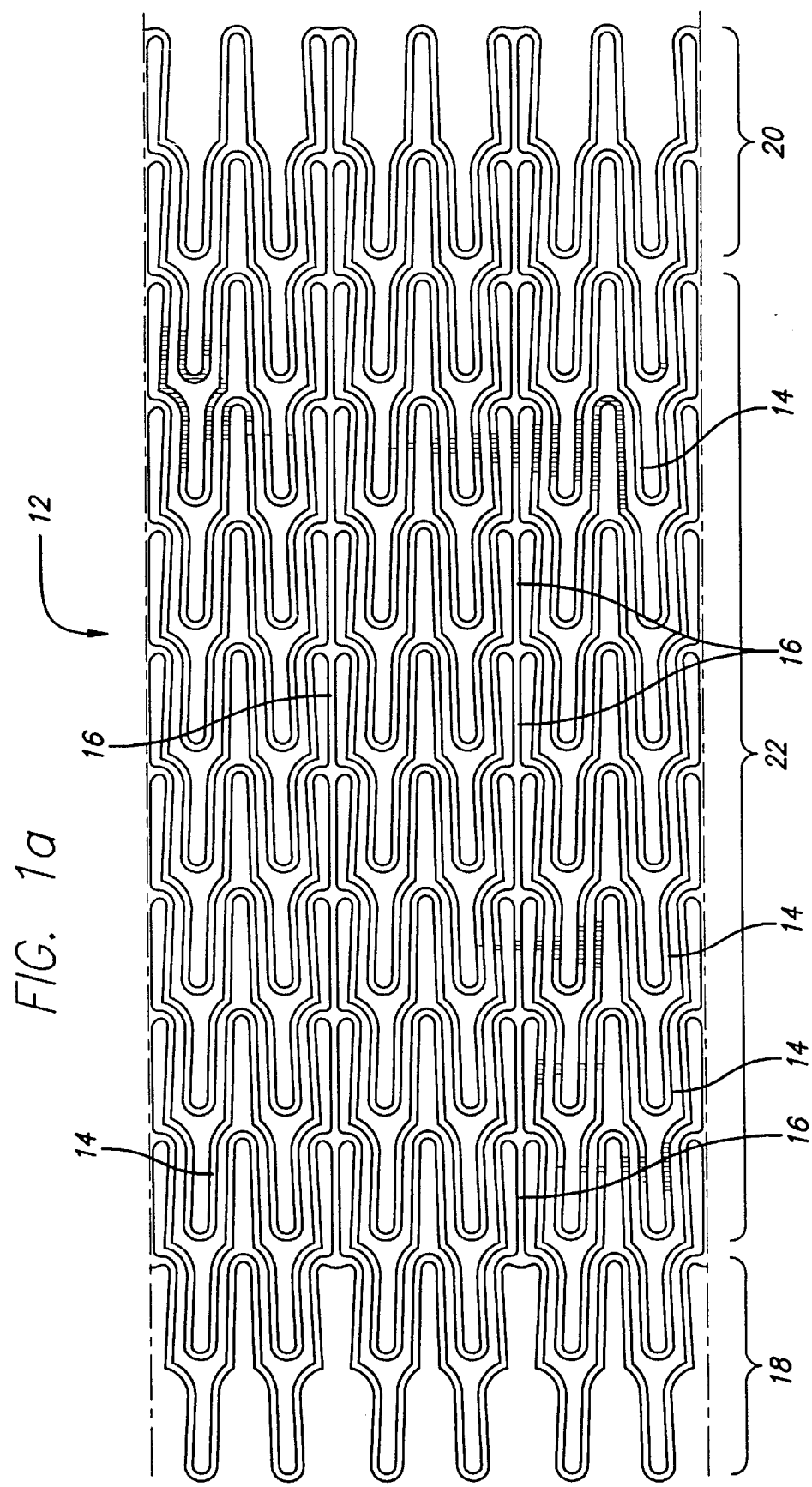
FIG. 1a illustrates a stent, the stiffness of which may be differentiated in accordance with the present invention.

FIG. 1a is a general depiction of a stent 12 showing a structure that includes struts 14 and spines 16. The struts open during expansion of the stent and serve to provide radial support to vessel walls. The spines maintain the struts in position relative to one another and serve to control foreshortening and flexibility of the stent in the longitudinal direction. The stent of the present invention is wholly formed of a superelastic material, preferably nitinol.

Preferably, the superelastic or shape memory alloy includes nickel-titanium (NiTi), however, other alloys also are contemplated. The shape memory characteristics allow the devices to be deformed to facilitate their insertion into a body lumen or cavity and then to be heated within the body so that the device returns to its original shape. Again, alloys having shape memory characterisitcs generally have at least two phases: a martensitic phase, which has a relatively low tensile strength and which is stable at relatively low temperatures, and an austenitic phase, which has a relatively high tensile strength and which is stable at temperatures higher than the martensitic phase.

Shape memory characteristics are imparted to the alloy by heating the metal to a temperature above which the transformation from the martensitic phase to the austenitic phase is complete; i.e., a temperature above which the austenitic phase is stable. The shape of the metal during this heat treatment is the shape "remembered." The heat-treated metal is cooled to a temperature at which the martensitic phase is stable, causing the austenitic phase to transform to the martensitic phase. The metal in the martensitic phase is then plastically deformed, e.g., to facilitate the entry thereof into a patient's body. Subsequent heating of the deformed martensitic phase to a temperature above the martensite to austenite transformation temperature causes the deformed martensitic phase to transform to the austenitic phase. During this phase transformation the metal reverts back to its original shape.

The recovery or transition temperature may be altered by making minor variations in the composition of the metal and in processing the material. In developing the correct composition, biological temperature compatibility must be determined in order to select the correct transition temperature. In other words, when the stent is heated, it must not be so hot that it is incompatible with the surrounding body tissue. Other shape memory materials may also be utilized, such as, but not limited to, irradiated memory polymers such as autocrosslinkable high density polyethylene (HDPEX).

Shape memory alloys are known in the art and are discussed in, for example, "Shape Memory Alloys," *Scientific American*, Vol. 281, pp. 74–82 (November 1979),.

Shape memory alloys undergo a transition between an austenitic state and a martinsitic state at certain temperatures. When they are deformed while in the martinsitic state they will retain this deformation as long as they are retained in this state, but will revert to their original configuration when they are heated to a transition temperature, at which time they transform to their austenitic state. The temperatures at which these transitions occur are affected by the nature of the alloy and the condition of the material. Nickel-titanium-based alloys (NiTi), wherein the transition temperature is slightly lower than body temperature, are preferred for the present invention. It is desirable to have the transition temperature set at just below body temperature to insure a rapid transition from the martinsitic state to the austenitic state when the stent is implanted in a body lumen.

Figure 1B:
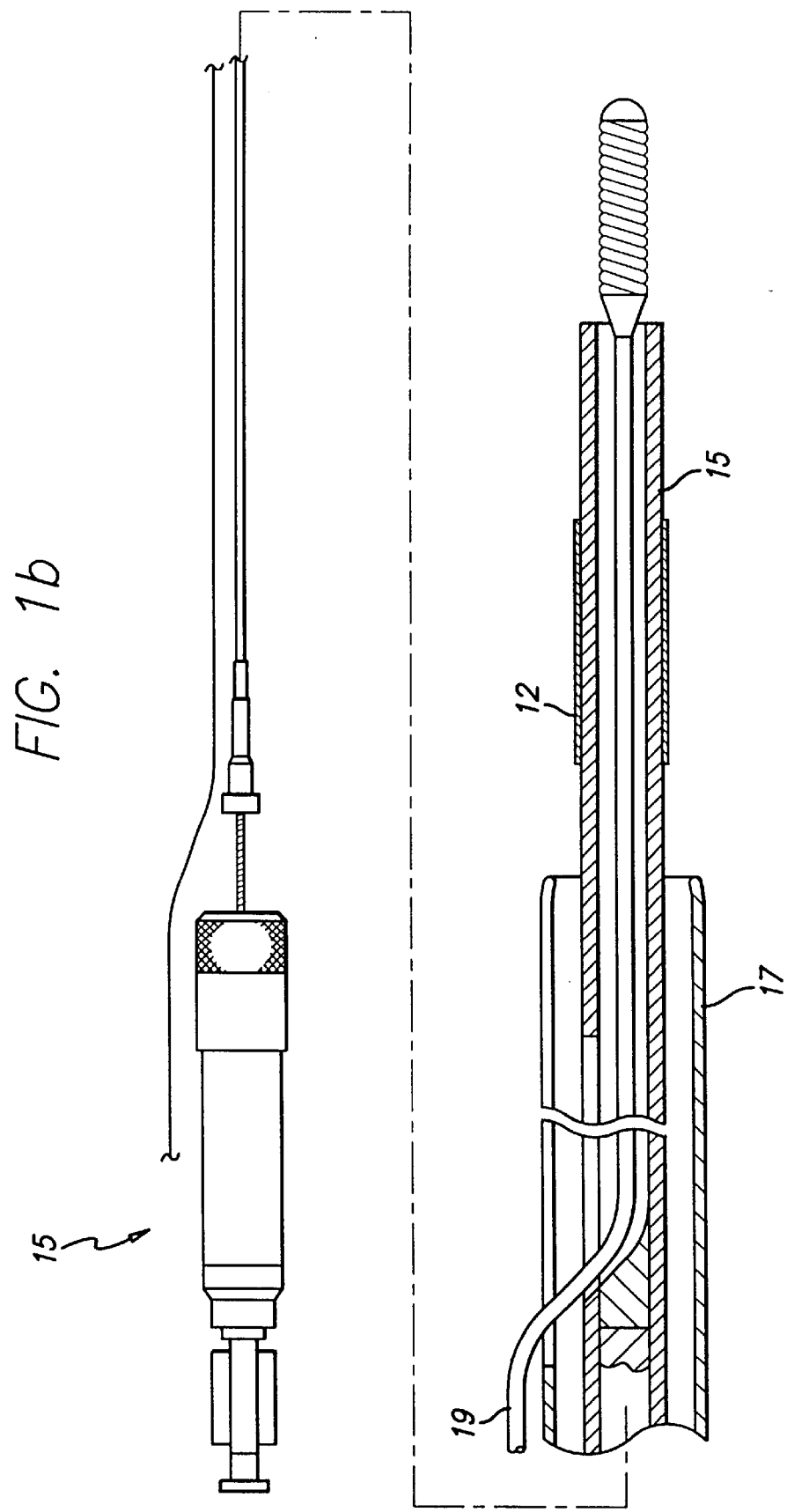
FIG. 1b illustrates the stent of the present invention mounted on a rapid-exchange catheter with a retractable sheath.
Figure 1C:
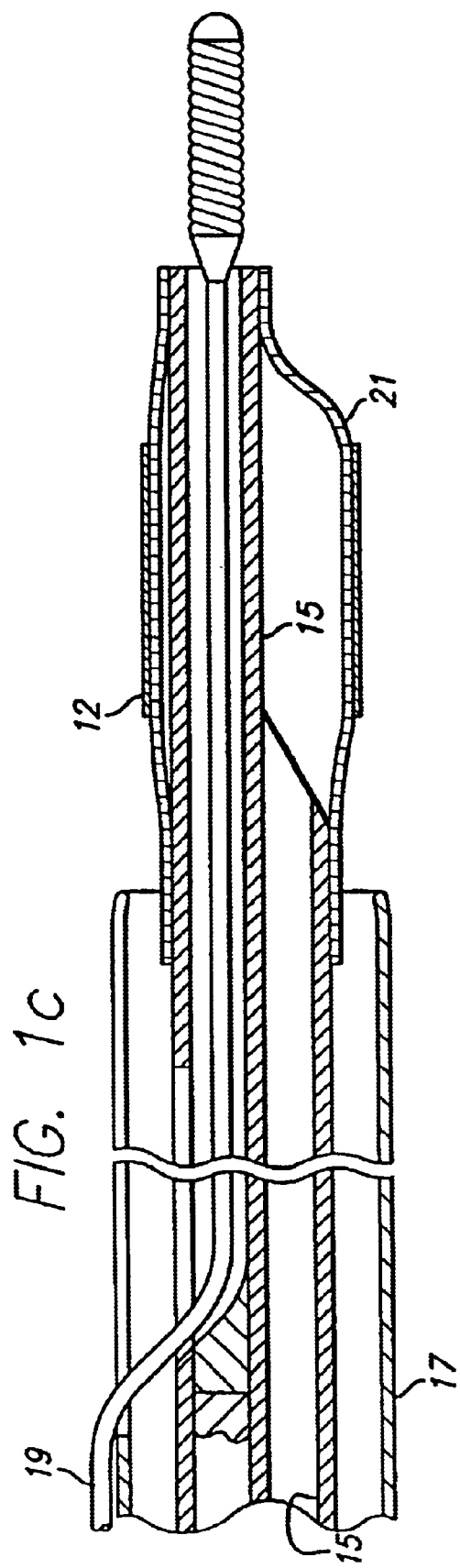
FIG. 1c illustrates the stent of the present invention mounted on a rapid-exchange balloon catheter with retractable sheath.

Referring to FIG. 1b, stent 12 is formed from a shape memory alloy, such as NiTi discussed above. After the stent is mounted on a catheter 15 and restrained by a sheath 17, the stent is inserted into an artery or other vessel by advancing the catheter over a guide wire 19. When the sheath is withdrawn, the stent then immediately expands due to contact with the higher temperature within the artery as described for devices made from shape memory alloys. Alternatively, as shown in FIG. 1c, the stent can be mounted on a balloon 21 and will be expanded at least in part by the balloon.

As is well known in the art, nitinol may undergo a transition from its martensitic phase to its austenitic phase under certain conditions including when its temperature is increased through a phase transition zone. The temperature at which the transition of martensite to austenite "starts" is referred to as the A(s) while the temperature at which its transformation to austenite is "finished" is commonly referred to as the A(f). While in its martensitic phase, the material is relatively in a soft and malleable state but upon heating becomes relatively stiffer and stronger as it approaches transition, transitions into its austenitic phase, and is heated beyond the A(f). The temperature range in which the transition occurs is affected by the heat energy that is absorbed during its heat treatment. A higher temperature and/or longer exposure to the heat treatment temperature will cause the A(f) to shift upwardly. A stent having a nitinol structure with an A(f) that has been shifted nearer to body temperature will cause the stent to be in a softer and more malleable state upon being deployed within the body than a stent formed of a nitinol structure with an A(f) at a lower temperature. Similarly, a stent having a nitinol structure with an A(f) that has been shifted beyond body temperature will cause the stent to be in a softer and more malleable state upon being deployed within the body than a stent having an A(f) that is closer to body temperature or below body temperature. The present invention provides for the selective adjustment of the A(f) in different areas or different individual elements of the same stent after its fabrication. Upon deployment, those areas or elements of the stent having a higher A(f) will be in a softer and more malleable state than areas or elements with a lower A(f). The reduced stiffness will cause the affected portion of the stent to exert less force in an effort to attain its set shape.

The stent of the present invention also may be of the pseudoelastic nitinol (or other pseudoelastic alloy), which exhibits stress-induced martinsite properties. In this embodiment, the nitinol stent may undergo a transition from its austenitic phase to its martinsitic phase by the application of stress. When the stress is removed, the alloy will transform from the martinsitic phase to the austenitic phase without a change in temperature (isothermally).

Figure 2A:
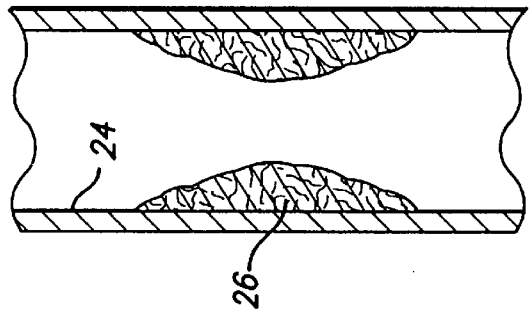
FIGS. 2a–c illustrate the deployment of a prior art stent and a stent of the present invention in the same stenosed vascular site.
Figure 2B:
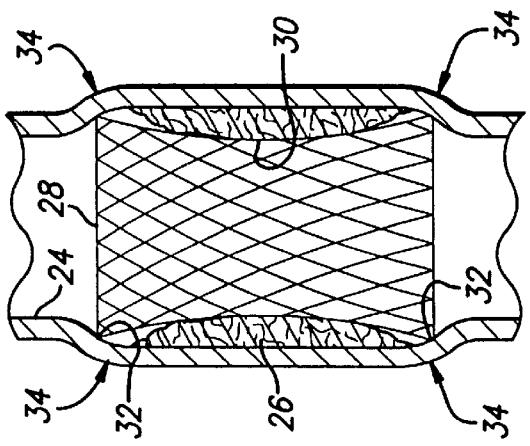
Figure 2C:
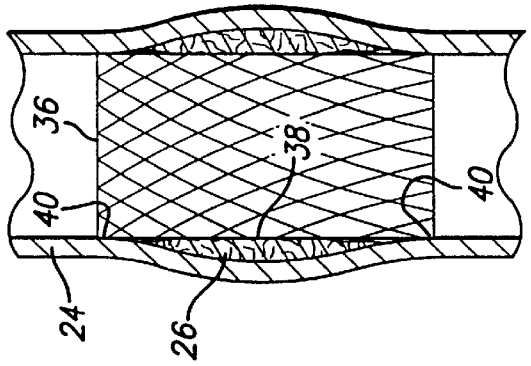

In one preferred embodiment, the ends 18, 20 of the stent are caused to be in a softer and more malleable state upon deployment than the center section 22 of the stent, both in terms of longitudinal stiffness as well as radial stiffness. Such configuration enables the stent to more closely conform to the contours of a particular deployment site and thereby reduces the risk that the ends of the stent will become deeply embedded in the vessel tissue thereby potentially causing injury. FIG. 2a is a cross-sectional view of a blood vessel 24 partial blocked by a stenosis 26. A prior art stent 28 of uniform stiffness is shown deployed at such site in FIG. 2b wherein its radial stiffness has been selected such that it is capable of exerting sufficient force against the stenosed section of the vessel to maintain the lumen at its full diameter throughout the stenosed site. While such force is sufficient to enable the center section 30 of the stent to maintain the vessel wall and associated stenosis properly expanded, the same force exerted by the stent ends 32 on the adjacent vessel wall without a stenosis has the undesirable effect of causing the ends of the stent to become more deeply embedded in the vessel tissue at 34. In FIG. 2c, a stent 36 of the present invention, having a differentiated stiffness, is shown deployed in the same site. The stiffer and stronger center section of the stent 38 is thereby able to maintain the vessel wall and stenosis sufficiently expanded to achieve full diameter while the softer and more malleable ends 40 conform to the vessel walls without becoming embedded therein.

Such differentiation can be achieved in a number of ways including for example by exclusively contacting the center portion of the stent with a heat sink during heat treatment. Less heat energy would thereby be transferred to the center section than to the end sections of the stent and as a consequence, the A(f) of the center section would remain lower than that of the end sections. By adjusting the A(f) of the center section to between approximately 0√ C. and 10° C. and that of the end sections to between approximately 20° C. and 30° C., an approximately 50% difference in flexibility can be achieved when the temperature of the stent is subsequently raised to 37° C. upon deployment in the human vasculature. A similar result can be attained by subjecting the ends to heating coils that would serve to transfer additional heat to the ends during the heat treatment process.

Figure 3A:
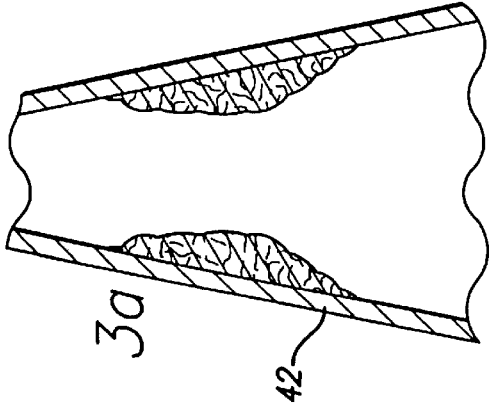
FIGS. 3a–c illustrate the deployment of a prior art stent and a stent of the present invention in the same tapered vascular site.
Figure 3B:
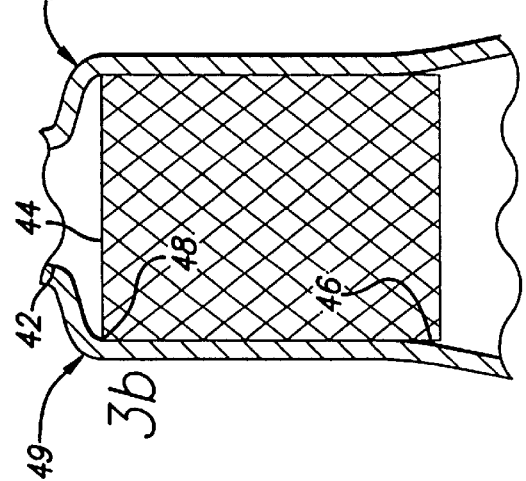
Figure 3C:
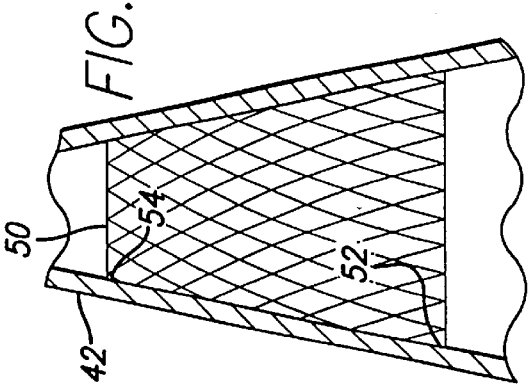

In another preferred embodiment of the present invention, one end of the stent is rendered softer and more malleable than the other in terms of longitudinal as well as radial stiffness. By gradually varying the stiffness along the entire length of the stent, the stent is able to more uniformly conform to a tapered deployment site. FIG. 3a depicts a blood vessel 42 having a tapered shape. FIG. 3b is a somewhat exaggerated illustration of a prior art stent 44 of uniform stiffness deployed in such vessel. While the stent is able to expand sufficiently for its one end 46 to engage and support the vessel wall, the other end 48 expands with the same amount of force and causes the much more restricted section of the blood vessel to deform at 49. In contrast thereto, a stent 50 of the present invention having had its stiffness differentiated such that end 52 is stiffer than end 54 will cause a more uniform force to be exerted against the tapered vessel. As a result, the end positioned in the more restricted section of the blood vessel is less likely to become embedded in the vessel tissue. A gradual variation of the stiffness along the entire length of stent enables a uniform force to be exerted on the vessel walls at all points of engagement.

Figure 4A:
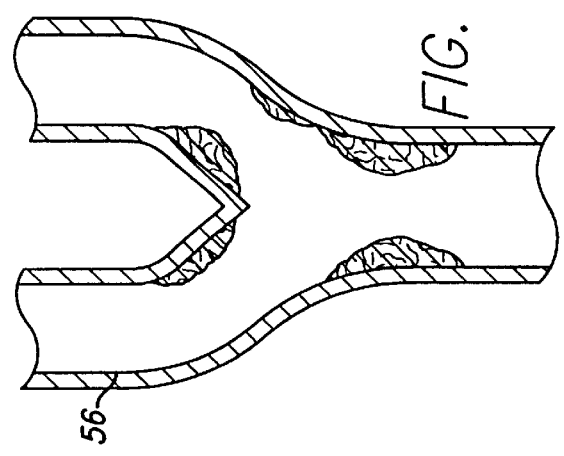
FIGS. 4a–c illustrate the deployment of a prior art stent and a stent of the present invention in the same bifurcated vascular site.
Figure 4B:
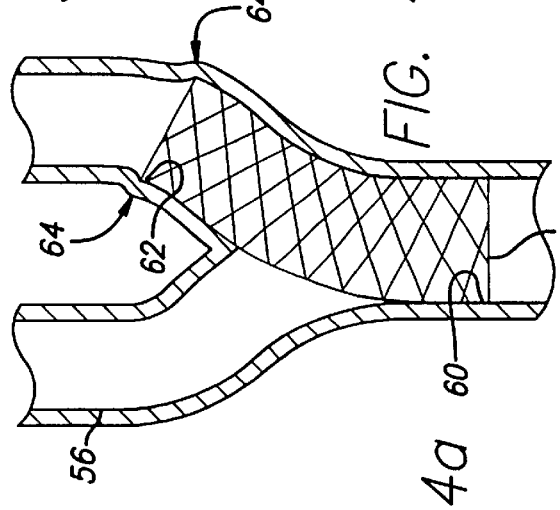
Figure 4C:
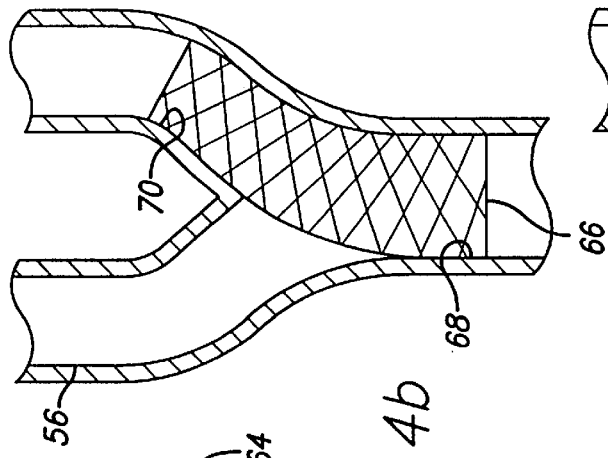

A stent of the present invention having had its stiffness differentiated such that one end is softer and more malleable than the other can also be advantageously employed for providing support across a bifurcation. For such application a more abrupt differentiation of the stent stiffness may be advantageous. FIG. 4a illustrates a bifurcated blood vessel 56. In FIG. 4b, a prior art stent 58 of uniform stiffness is shown in its deployed state. One of its ends 60 expands to engage and support the larger diameter of the single vessel while the other end 62 expands with the same force against the smaller diameter branch which causes such end to become embedded in the vessel tissue at 64. Stent 66, having had its stiffness differentiated in accordance with the present invention such that one end 68 is in a stiffer state than the other end 70, is able to support the bifurcation without causing the end positioned in the smaller lumen to become embedded in the vessel tissue.

Such stiffness differentiation is achieved by transferring a differentiated amount of heat energy to selected portions of the stent in any of a number of ways including with the use of an advantageously positioned heat sink or with the use of an auxiliary heat source. The change in the A(f) may be spread over a very short section of the stent or alternatively, a substantial portion thereof if for example a gradual taper is desired. The heat sink, or alternatively, the auxiliary heat source would have to be configured so as to achieve the desired heating or cooling gradient.

Figure 5A:
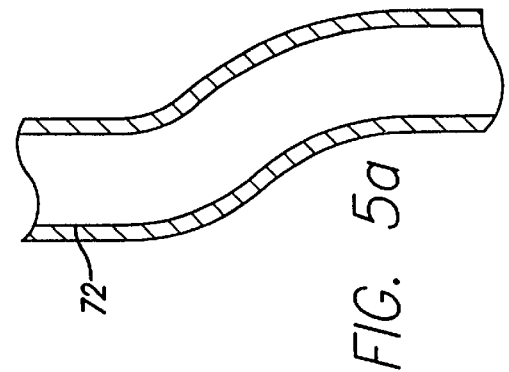
FIGS. 5a–c illustrate the deployment of a prior art stent and a stent of the present invention in the same non-linear vascular site.
Figure 5B:
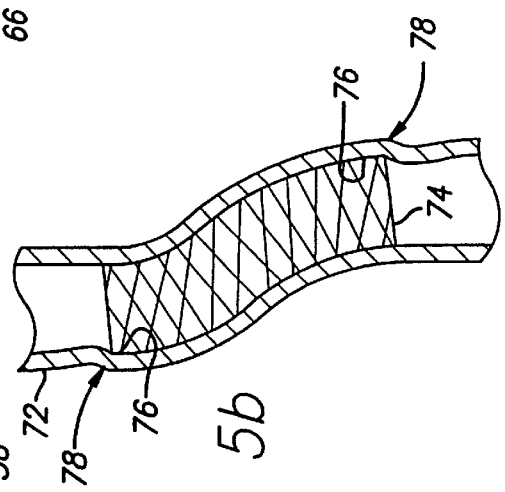
Figure 5C:
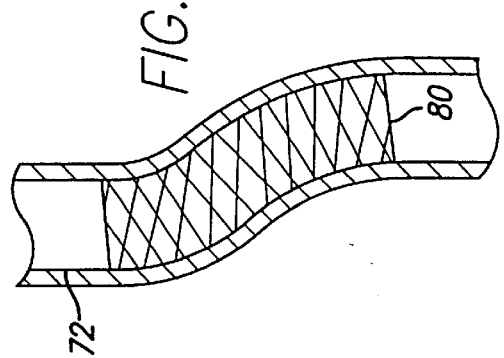

In a further alternative embodiment of the present invention, only the spines 16 of the stent 12 are caused to assume a softer and more malleable while the struts 14 remain in a relatively stiff state. This yields a stent having reduced longitudinal stiffness combined with a relatively high degree of radial stifffness. Such a stent is substantially more capable of conforming to a non-linear deployment site to provide desired support while reducing the likelihood of portions of its ends becoming more deeply embedded in the vessel tissue. FIG. 5a illustrates a non-linear deployment site 72 while FIG. 5b illustrates a prior art stent 74 deployed therein. Because the longitudinal stifffness of the structure causes it to resist bending, the outboard sides 76 of the stent ends will cause more force to be exerted against the vessel walls than at all other points along the length of the stent when the stent is forced to conform to a non-linear site. Consequently those sections of the stent ends will tend to become more deeply embedded in the vessel tissue. FIG. 5c on the other hand, illustrates a stent 80 deployed at such site, wherein the stiffness of the stent has been differentiated in accordance with the present invention such that its longitudinal stiffniess has been reduced vis-a-vis its radial stifff- ness. As a result less force is exerted on the vessel walls in response to the non-linearity and its ends will be less likely to become so deeply embedded in the vessel tissue.

Differentiation of the longitudinal stiffness relative to the radial stiffness may be achieved by focusing a laser on each of the spine sections 16 of the stent. Use of a laser allows the transfer of heat energy to be confined to very isolated areas and thus allows the A(f) of the spines to be shifted without affecting the A(f) of the struts. By alternatively treating only the spines near the ends of the stent, the longitudinal stiffness is not only differentiated with respect to the radial stiffness of the stent but also with respect to the longitudinal stiffness of the center section of the stent.

A stent with differentiated stiffniess is deployed in the usual manner and a number of delivery devices and methods are well known. The stent is carried about a delivery catheter in its collapsed state and introduced into the vasculature through which it is advanced to the deployment site. Once in position, the stent is allowed to expand by retracting a restraining sheath after which an underlying balloon may be employed to post-dilate the site. Once fully deployed, all delivery equipment is removed and the stent remains in place to support the vessel walls. Other stent delivery catheters and methods of delivery are known in the art. As the stent is heated to body temperature, those sections having a relatively lower A(f) will attempt to attain their set shape more forcefully than sections with a higher A(f) wherein the advantageous selection of the A(f)s as exemplified above will result in a more uniform force distribution at the deployment site.

While a particular form of the invention has been illustrated and described, it will also be apparent to those skilled in the art that various modifications can be made without departing from the spirit and scope of the invention. More particularly, the invention is not limited to any one particular stent configuration nor to any particular stent application. Moreover, invention is not limited to the use of any particular superelastic material nor to any particular pattern of high and low A(f) distribution. Accordingly, it is not intended that the invention be limited except by the appended claims.

What is claimed:

1. A stent formed of a superelastic material, wherein such material transitions between a relatively soft and malleable phase and a relatively stiff phase at an adjustable transition temperature and wherein such stent is differentiated in terms of the transition temperature to which selected portions thereof have been adjusted such that the stent assumes a tapered configuration upon expansion whereby one end of the stent assumes a softer and more malleable state relative to the opposite end of the stent when the stent is subjected to body temperature.

2. The stent of claim 1, wherein the transition temperatures of all portions of the stent are below body temperature.

3. The stent of claim 1, wherein the transition temperatures of certain portions of the stent are below body temperature while other portions of the stent have a transition temperatures above body temperature.

4. The stent of claim 1, wherein the transition temperatures of all portions of the stent are above body temperature.

5. The stent of claim 1, wherein one end portion of the stent has a higher transition temperature than the opposite end portion of the stent, whereby the one end portion of the stent assumes relatively stiffer state than the opposite end portion of the stent when the stent is subjected to body temperature.

6. The stent of claim 5, wherein the transition temperature gradually increases along the stent from one end portion to the opposite end portion.

7. The stent of claim 5, wherein the transition temperature abruptly increases at a point between the one end portion and the opposite end portion of the stent.

8. The stent of claim 1, wherein the stent comprises a structure of struts and spines wherein the struts extend about the circumference of the stent and expand upon deployment of the stent and the spines extend along a length of the stent and do not distort upon deployment, wherein selected spines have a higher transition temperature than the struts whereby the longitudinal stiffness of the stent is reduced without a commensurate reduction in radial stiffness upon being subjected to body temperature.

9. The stent of claim 8, wherein all of the spines have a higher transition temperature than the struts.

10. A The stent of claim 1, wherein the superelastic material is nitinol which undergoes a transition from its martensitic phase to its austenitic phase as its temperature is increased through a transition zone and wherein A(f) designates the temperature at which such transition is completed.

11. The stent of claim 10, wherein the A(f) transition temperature of selected portions of the stent is about 20° C.

higher than other portions of the stent, whereby an approximately 50% difference in stiffness is achieved when the stent is subjected to body temperature.

12. The stent of claim 11, wherein the A(f) transition temperature of selected portions of the stent is 0° C. to 10° C. while other portions of the stent have an A(f) transition temperature of 20° C. to 30° C.

13. A method of manufacturing a stent having a structure of differentiated stiffness, comprising:
constructing a stent of superelastic material, wherein such material transitions between a relatively soft and malleable phase and a relatively stiff phase at an adjustable transition temperature and wherein the adjustable transition temperature is increased upon absorbing heat energy during heat treatment; and
transferring differentiated amounts of heat energy to selected portions of the stent during heat treatment to differentially adjust the transition temperature of the portions such that the stent assumes a tapered configuration upon expansion.

14. The method of claim 13, wherein differentiated amounts of heat energy are transferred to selected portions of the stent by only contacting the selected portions with a heat source.

15. The method of claim 13, wherein differentiated amounts of heat energy are transferred to selected portions of the stent by maintaining only the selected portions of the stent in contact with a heat sink while heating the stent.

16. The method of claim 13, wherein the differentiated amounts of heat energy are transferred to selected portions of the stent by focusing a laser on the selected portions.

17. The method of claim 13, wherein the stent includes a plurality of struts that extend about the circumference of the stent and undergo expansion during deployment of the stent and a plurality of spines that extend along the length of the stent and do not distort upon deployment of the stent, wherein the laser is only focused on selected spines whereby the longitudinal stiffness of the stent is reduced without reducing radial stiffness.

18. The method of claim 17, wherein the laser is focused on all spines.

19. A stent formed of a superelastic material, wherein such material transitions between a relatively soft and malleable phase and a relatively stiff phase at an adjustable transition temperature, comprising:
a first portion of said stent, having a transition temperature adjusted so as to cause said first portion to be in a relatively stiff state when said stent is subjected to body temperature, wherein said first portion includes one end of the stent; and
a second portion of said stent, having a transition temperature adjusted so as to cause said second portion to be in a relatively softer and more malleable state when said stent is subjected to body temperature, wherein said second portion includes an opposite end of the stent such that said stent assumes a tapered shape upon expansion.

20. The stent of claim 19, wherein all portions of said stent have transition temperatures that are below body temperature.

21. The stent of claim 19, wherein said transition temperature of said first portion is below body temperature and said transition temperature of said second portion is above body temperature.

22. The stent of claim 19, wherein all portions of said stent have transition temperatures that are above body temperature.

23. The stent of claim 19, wherein the transition temperature of said material gradually increases along said stent between said first portion and said second portion.

24. The stent of claim 19, wherein the transition temperature of said material abruptly changes between said first portion and said second portion.

25. A stent formed of a superelastic material, wherein such material transitions between a relatively soft and malleable phase and a relatively stiff phase at an adjustable transition temperature, comprising:
struts that extend about the circumference of said stent and expand upon deployment, wherein said struts have transition temperatures selected so that struts at one end of the stent are in a relatively soft and malleable state and the struts at the other end are in a relatively stiff state such that said stent assumes a tapered shape upon expansion when said stent is subjected to body temperature; and
spines that extend along a length of the stent and do not distort upon deployment of said stent, wherein selected spines have a transition temperature so as to cause said spines to be in a relatively softer and more malleable state when said stent is subjected to body temperature.

26. The stent of claim 25, wherein all of said spines have a transition temperature that is higher than said transition temperature of said struts.

27. A tapered stent formed of a superelastic material, wherein such material transitions between a relatively soft and malleable phase and a relatively stiff state at an adjustable transition temperature, comprising:
a first end of said stent, wherein said material has a transition temperature adjusted so as to cause said first end to be in a relatively stiff phase when said stent is subjected to body temperature and wherein said first end assumes a relatively small diameter upon deployment; and
a second end of said stent, wherein said material has a transition temperature adjusted so as to cause said second end to be in a relatively softer and more malleable state when said stent is subjected to body temperature and wherein said second end assumes a relatively large diameter upon deployment.

28. The stent of claim 27, wherein said transition temperature of said stent material gradually changes between said first and second end.

29. The stent of claim 27, wherein said transition temperature of said stent material abruptly changes between said first and second end.

30. The stent of claim 27, wherein said transition temperatures of both ends of said stent are below body temperature.

31. The stent of claim 27, wherein said transition temperatures of both ends of said stent are all above body temperature.

32. The stent of claim 27, wherein said transition temperature of said first end is below body temperature and said transition temperature of said second end is above body temperature.

33. A stent that upon deployment assumes a tapered shape having a large end and a small end, wherein such stent is formed of a superelastic material and wherein such material transitions between a relatively soft and malleable phase and a relatively stiff phase at an adjustable transition temperature, comprising:
a first portion of said stent, wherein said material has a transition temperature adjusted so as to cause said first portion to be in a relatively stiff state when said stent is subjected to body temperature and wherein said first portion defines said small end of said tapered shape upon deployment; and a second portion of said stent, wherein said material has a transition temperature adjusted so as to cause said second portion to be in a relatively softer and more malleable state when said stent is subjected to body temperature; and wherein said second portion defines said large end of said tapered shape upon deployment.

34. The stent of claim 33, wherein said transition temperature of said stent material gradually changes between said first and second portion.

35. The stent of claim 33, wherein said transition temperature of said stent material abruptly changes between said first and second portion.

36. The stent of claim 33, wherein all portions of said stent have transition temperatures below body temperature.

37. The stent of claim 33, wherein said transition temperatures of said stent are all above body temperature.

38. The stent of claim 33, wherein said transition temperature of said first portion is below body temperature and said transition temperature of said second portion is above body temperature.

* * * * *

UNITED STATES PATENT AND TRADEMARK OFFICE
CERTIFICATE OF CORRECTION

PATENT NO. : 6,652,576 B1
DATED : November 25, 2003
INVENTOR(S) : Kent C.B. Stalker It is certified that error appears in the above-identified patent and that said Letters Patent is hereby corrected as shown below:

Column 1,
Line 39, change "stiffniess" to -- stiffness --

Column 2,
Lines 2 and 20, change "stiffniess" to -- stiffness --

Column 3,
Line 17, change "stiffniess" to -- stiffness --

Column 4,
Lines 10 and 11, change "stiffniess" to -- stiffness --
Line 65, delete "." after "1979)," and insert -- incorporated herein by reference. --

Column 6,
Line 33, change "0√ C." to -- 0° C. --

Column 7,
Lines 45 and 46, change "stifffness" to -- stiffness --
Line 59, change "stiffniess" to -- stiffness --

Column 11,
Line 9, change "temperature:" to -- temperature --

Signed and Sealed this

Second Day of March, 2004

JON W. DUDAS
*Acting Director of the United States Patent and Trademark Office*